(12) United States Patent
Israel

(10) Patent No.: US 11,826,379 B2
(45) Date of Patent: Nov. 28, 2023

(54) METHODS AND COMPOSITIONS FOR TREATMENT OF COVID-19

(71) Applicant: Esrail Medical Corp., Beverly Hills, CA (US)

(72) Inventor: Rafi Israel, Beverly Hills, CA (US)

(*) Notice: Subject to any disclaimer, the term of this patent is extended or adjusted under 35 U.S.C. 154(b) by 0 days.

(21) Appl. No.: 17/936,379

(22) Filed: Sep. 28, 2022

(65) Prior Publication Data

US 2023/0022162 A1    Jan. 26, 2023

Related U.S. Application Data

(63) Continuation-in-part of application No. PCT/US2021/024745, filed on Mar. 29, 2021.

(60) Provisional application No. 63/001,284, filed on Mar. 28, 2020.

(51) Int. Cl.
| | | |
|---|---|---|
| *A01N 43/04* | (2006.01) | |
| *A61K 31/70* | (2006.01) | |
| *A61K 31/7056* | (2006.01) | |
| *A61P 31/14* | (2006.01) | |
| *A61K 31/65* | (2006.01) | |

(52) U.S. Cl.
CPC .......... *A61K 31/7056* (2013.01); *A61K 31/65* (2013.01); *A61P 31/14* (2018.01)

(58) Field of Classification Search
None
See application file for complete search history.

(56) References Cited

PUBLICATIONS

Li, Guangdi, and Erik De Clercq. "Therapeutic options for the 2019 novel coronavirus (2019-nCoV)." Nature reviews Drug discovery 19.3 (2020): 149-150.*

Chaudhury et al. Journal of Herbal Medicine (2018), vol. 14, pp. 22-28.*

* cited by examiner

*Primary Examiner* — Patrick T Lewis
(74) *Attorney, Agent, or Firm* — Umair A. Qadeer

(57) ABSTRACT

A method of treatment for coronavirus disease 2019 (COVID-19) is disclosed herein. The method comprises administering a therapeutically effective dose of a combination of ribavirin and minocycline. A pharmaceutical composition comprising ribavirin and minocycline is also disclosed herein. The pharmaceutical composition may further include one or more pharmaceutical excipients.

8 Claims, No Drawings

METHODS AND COMPOSITIONS FOR TREATMENT OF COVID-19

CROSS-REFERENCE TO RELATED APPLICATIONS

This application is a continuation-in-part of PCT Patent Application No. PCT/US2021/024745, filed on Mar. 29, 2021, which claims the benefit of U.S. Provisional Patent Application Ser. No. 63/001,284, filed on Mar. 28, 2020, the disclosures of which are hereby incorporated in their entireties herein by reference.

BACKGROUND

Field of the Invention

The present disclosure relates to methods and compositions for treatment of coronavirus disease 2019 (COVID-19).

Description of the Related Art

Coronavirus disease 2019 (COVID-19) is an infectious disease caused by severe acute respiratory syndrome coronavirus 2 (SARS-CoV-2). The disease was first identified in 2019 in Wuhan, China and has since spread globally, resulting in the 2019-21 coronavirus pandemic. Frequently observed symptoms of COVID-19 include fever, cough, and shortness of breath. While the majority of cases result in mild symptoms, some progress to pneumonia and multi-organ failure occurs. As of Mar. 29, 2021, COVID-19 has resulted in over 2.7 million deaths across the world, and the overall mortality rate for diagnosed cases is approximately 2.2 percent. See "Coronavirus Resource Center," Center for Systems Science and Engineering at Johns Hopkins University (available at: https://coronavirus.jhu.edu). However, the mortality rate ranges widely and depends on a variety of factors. See "Weekly Updates by Select Demographic and Geographic Characteristics," Centers for Disease Control and Prevention (available at: https://www.cdc.gov/nchs/nvss/vsrr/covid_weekly/index.htm).

Although multiple vaccines for COVID-19 have been granted emergency use authorization in several countries, it is possible that there will not be a sufficient supply of vaccines for the global population until sometime in 2022. See Irwin, A. "What It Will Take to Vaccinate the World Against COVID-19," *Nature*, 2021, doi: 10.1038/d41586-021-00727-3. In addition, it is unclear whether COVID-19 herd immunity will be practically attainable. See Aschwanden, C. "Five Reasons Why COVID Herd Immunity Is Probably Impossible," *Nature*, 2021, 591, 520-22, doi: 10.1038/d41586-021-00728-2. Almost 90 percent of immunologists, infectious disease specialists, and virologists in a survey conducted by *Nature* concluded that COVID-19 is likely to become endemic. See Phillips, N. "The Coronavirus Is Here to Stay—Here's What That Means," *Nature*, 2021, 590, 382-84, doi: 10.1038/d41586-021-00396-2.

Thus there remains an acute need for effective treatments for COVID-19.

SUMMARY

A method of treatment for coronavirus disease 2019 (COVID-19) is disclosed herein. The method comprises administering a therapeutically effective dose of a combination of ribavirin and minocycline. A pharmaceutical composition comprising ribavirin and minocycline is also disclosed herein. The pharmaceutical composition may further include one or more pharmaceutical excipients.

DETAILED DESCRIPTION

A method of treatment for coronavirus disease 2019 (COVID-19) is disclosed herein. The method comprises administering a therapeutically effective dose of a combination of ribavirin and minocycline. In some embodiments, the combination of ribavirin and minocycline may be administered as a composition that includes ribavirin and minocycline. In other embodiments, the combination of ribavirin and minocycline may be administered in distinct steps, where ribavirin and minocycline are administered separately in any order.

A pharmaceutical composition comprising ribavirin and minocycline is also disclosed herein. The pharmaceutical composition may further include one or more pharmaceutical excipients.

Ribavirin, also known as tribavirin, is an antiviral that is used to treat respiratory syncytial virus (RSV) infections, hepatitis C, hepatitis E, and some viral hemorrhagic fevers. See, e.g., "Ribavirin," Drugs.com (available at: https://www.drugs.com/monograph/ribavirin.html). Ribavirin is a guanosine (ribonucleic) analog used to prevent viral RNA synthesis and viral mRNA capping, and it is thus a nucleoside inhibitor. Ribavirin is a prodrug, and the relevant metabolites thereof resemble purine RNA nucleotides. In this form, the metabolites interfere with RNA metabolism required for viral replication.

The carboxamide group of ribavirin may cause the native nucleoside drug to resemble adenosine or guanosine. When ribavirin is incorporated into RNA as a base analog of either adenine or guanine, it thus pairs equally well with either uracil or cytosine. This may induce mutations in RNA-dependent replication in RNA viruses. Such hypermutation may be lethal to RNA viruses. See, e.g., Ortega-Prieto, A. M., et al. "Extinction of Hepatitis C Virus by Ribavirin in Hepatoma Cells Involves Lethal Mutagenesis," *PLoS One*, 2013, 8(8), e71039, doi: 10.1371/journal.pone.0071039; Crotty, S., et al. "Ribavirin's Antiviral Mechanism of Action: Lethal Mutagenesis?" *J. Mol. Med.* 2002, 80(2), 86-95, doi: 10.1007/s00109-001-0308-0.

Ribavirin is being studied separately as a possible component in a combination therapy for COVID-19. See "Lopinavir/Ritonavir, Ribavirin and IFN-beta Combination for nCoV Treatment," The University of Hong Kong, 2020, Clinical Trial Record No. NCT04276688 (available at: https://clinicaltrials.gov/ct2/show/NCT04276688).

Minocycline is a second-generation semi-synthetic derivative of tetracycline and has well-known anti-bacterial effects. Minocycline has also been shown to have antiviral activity in vitro and in some animal models. See Nagarakanti, S., et al. "Is Minocycline an Antiviral Agent? A Review of Current Literature," *Basic Clin. Pharmacol. Toxicol.* 2016, 118(1), 4-8, doi: 10.1111/bcpt.12444. Minocycline also has anti-inflammatory and anti-apoptosis effects and exhibits immune modulatory activity. See, e.g., Popovic, N., et al. "Inhibition of Autoimmune Encephalomyelitis by a Tetracycline," Ann. Neurol. 2002, 51, 215-23; Song, Y., et al., "Minocycline Protects PC12 Cells from Ischemic-Like Injury and Inhibits 5-Lipoxygenase Activation," *Neuroreport.* 2004, 15, 2181-4. Antiviral activity of minocycline has been described against HIV, Simian Immunodeficiency Virus (SIV), Japanese encephalitis virus (JEV), West Nile virus (WNV), Human T-lymphocytic virus type-1 (HTLV- 1), Sindbis, Rabies, and Reoviruses. See, e.g., Nagarakanti, S., et al., supra; Lemaitre, M., et al. "Protective Activity of Tetracycline Analogs Against the Cytopathic Effect of the Human Immunodeficiency Viruses in CEM Cells," *Res. Virol.* 1990, 141, 5-16.

In addition to inhibiting viral replication in the lungs and other tissues of patients with COVID-19, it is hypothesized that the combination of ribavirin and minocycline will provide anti-microbial effects to prevent secondary bacterial infections, anti-inflammatory effects to prevent fibrosis of lung tissue, and anti-apoptosis effects to prevent alveolar cell death. This provides the immune system of a patient with COVID-19 an opportunity to respond to the infection and build immunity against the SARS-CoV-2 virus.

In some embodiments, a composition including an amount of ribavirin between 1 mg and 1200 mg and an amount of minocycline between 10 mg and 400 mg may be administered to a patient with COVID-19. In some preferred embodiments, a composition including an amount of ribavirin between 5 mg and 200 mg and an amount of minocycline between 50 mg and 150 mg may be administered to a patient with COVID-19. In some more preferred embodiments, a composition including an amount of ribavirin between 5 mg and 100 mg and an amount of minocycline between 80 mg and 120 mg may be administered to a patient with COVID-19. In some even more preferred embodiments, a composition including an amount of ribavirin between 9 mg and 55 mg and an amount of minocycline between 90 mg and 110 mg may be administered to a patient with COVID-19. In some still more preferred embodiments, a composition including an amount of ribavirin between 15 mg and 30 mg and an amount of minocycline between 90 mg and 110 mg may be administered to a patient with COVID-19.

In some embodiments, an amount of ribavirin between 1 mg and 1200 mg and an amount of minocycline between 10 mg and 400 mg may be separately administered in any order to a patient with COVID-19. In some preferred embodiments, an amount of ribavirin between 5 mg and 200 mg and an amount of minocycline between 50 mg and 150 mg may be separately administered in any order to a patient with COVID-19. In some more preferred embodiments, an amount of ribavirin between 5 mg and 100 mg and an amount of minocycline between 80 mg and 120 mg may be separately administered in any order to a patient with COVID-19. In some even more preferred embodiments, an amount of ribavirin between 9 mg and 55 mg and an amount of minocycline between 90 mg and 110 mg may be separately administered in any order to a patient with COVID-19. In some still more preferred embodiments, an amount of ribavirin between 15 mg and 30 mg and an amount of minocycline between 90 mg and 110 mg may be separately administered in any order to a patient with COVID-19.

In some embodiments, the combination of ribavirin and minocycline may be administered orally to a patient with COVID-19. In some preferred embodiments, the disclosed combination may be administered orally to a patient with COVID-19 twice daily. In some alternate embodiments, the combination of ribavirin and minocycline may be administered intravenously to a patient with COVID-19.

A composition that includes an amount of ribavirin between 1 mg and 1200 mg and an amount of minocycline between 10 mg and 400 mg is also disclosed herein. In some preferred embodiments, the composition may include an amount of ribavirin between 5 mg and 200 mg and an amount of minocycline between 50 mg and 150 mg. In some more preferred embodiments, the composition may include an amount of ribavirin between 5 mg and 100 mg and an amount of minocycline between 80 mg and 120 mg. In some even more preferred embodiments, the composition may include an amount of ribavirin between 9 mg and 55 mg and an amount of minocycline between 90 mg and 110 mg. In some still more preferred embodiments, the composition may include an amount of ribavirin between 15 mg and 30 mg and an amount of minocycline between 90 mg and 110 mg. The composition may further include one or more pharmaceutical excipients.

In some embodiments, the composition may be dissolved in a suitable solvent. The composition may be administered to a patient orally or intravenously.

The disclosed treatment is suitable for use in treatment of COVID-19 infections caused by existing and novel variants of SARS-CoV-2.

SUMMARY OF TRIALS

A total of sixty-eight (68) patients having COVID-19, as determined by positive PCR test results, were treated using a combination of 25 mg ribavirin and 100 mg minocycline. The treatment protocol for each of these patients was oral administration of a capsule containing a composition that included 25 mg ribavirin and 100 mg minocycline to the patient twice daily for seven days. Three patients in the trial were hospitalized with severe COVID-19 prior to starting treatment, and all three improved after treatment such that they no longer required hospitalization. All patients became afebrile within three days of starting treatment. The most commonly observed side effect was nausea, which was treated concurrently with meclizine or ondansetron in thirty-two (32) patients. No serious adverse reactions to treatment were observed.

A total of forty-two (42) patients having COVID-19, as determined by positive PCR or antigen test results, were treated using a combination of 20 mg ribavirin and 100 mg minocycline. The treatment protocol for each of these patients was oral administration of a capsule containing a composition that included 20 mg ribavirin and 100 mg minocycline to the patient twice daily for seven days. The lower dosage of ribavirin reduced the incidence of nausea as a side effect, without reducing the efficacy of the treatment.

A total of about twelve (12) patients confirmed to have COVID-19, as determined by positive PCR test results, or suspected of having COVID-19 were treated using a combination of 10 mg ribavirin and 100 mg minocycline. The treatment protocol for each of these patients was oral administration of a capsule containing a composition that included 10 mg ribavirin and 100 mg minocycline to the patient twice daily for five, seven, or ten days.

Patients who also received treatment with acetaminophen, propranolol, nebivolol, benzonatate and/or albuterol prior to or during treatment with a combination of ribavirin and minocycline experienced no observed adverse effects from the treatment.

Exemplary Case Studies

A sixty-three year old female patient who had tested positive for COVID-19 via PCR was treated using a combination of ribavirin and minocycline. The patient had a severe cough, a fever above 102 degrees Fahrenheit, and severe shortness of breath when the treatment was started. A capsule containing a composition that included 25 mg ribavirin and 100 mg minocycline was orally administered to the patient twice daily for seven days. The patient was also administered acetaminophen as needed. The patient was afebrile within two days, and the patient's cough and shortness of breath decreased significantly within three days. The patient was fully recovered within seven days after starting treatment.

A fifty-nine year old male patient who had tested positive for COVID-19 via PCR was treated using a combination of ribavirin and minocycline. The patient had a severe cough, a fever above 103 degrees Fahrenheit, and severe fatigue and body aches when the treatment was started. A capsule containing a composition that included 25 mg ribavirin and 100 mg minocycline was orally administered to the patient twice daily for seven days. The patient was also administered acetaminophen as needed. The patient was afebrile within three days, and the patient's cough decreased substantially within two days. The patient was fully recovered with the exception of a mild cough within seven days after starting treatment.

A seventy-three year old male patient who had tested positive for COVID-19 via PCR was treated using a combination of ribavirin and minocycline. The patient had a severe cough, a fever above 102 degrees Fahrenheit, severe shortness of breath, and severe fatigue and body aches when the treatment was started. A capsule containing a composition that included 25 mg ribavirin and 100 mg minocycline was orally administered to the patient twice daily for seven days. The patient was also administered acetaminophen as needed. The patient was afebrile within three days, the patient's cough decreased substantially within four days, and the patient's shortness of breath was substantially improved within five days. The patient recovered within seven days after starting treatment.

A seventy-eight year old female patient who had tested positive for COVID-19 via PCR was treated using a combination of ribavirin and minocycline. The patient had a moderate cough, a fever above 103 degrees Fahrenheit, shortness of breath, severe fatigue, and abdominal pain when the treatment was started. A capsule containing a composition that included 25 mg ribavirin and 100 mg minocycline was orally administered to the patient twice daily for seven days. The patient was also administered acetaminophen as needed. The patient was afebrile within two days, the patient's cough decreased significantly and abdominal pain was resolved within five days, and the patient experienced only minimal shortness of breath after six days. The patient was almost fully recovered within seven days after starting treatment.

A forty-three year old female patient who had tested positive for COVID-19 via PCR was treated using a combination of ribavirin and minocycline. The patient had a severe cough, a fever above 103 degrees Fahrenheit, and extreme weakness when the treatment was started. A capsule containing a composition that included 25 mg ribavirin and 100 mg minocycline was orally administered to the patient twice daily for seven days. The patient was also administered albuterol by inhaler and acetaminophen as needed. The patient was afebrile within two days, and the patient's cough decreased significantly within three days. The patient was fully recovered within seven days after starting treatment.

A fifty year old female patient who had tested positive for COVID-19 via PCR and was hospitalized therefor was treated using a combination of ribavirin and minocycline. The patient had a severe cough, a high fever, shortness of breath, abdominal pain, and extreme fatigue when the treatment was started. A capsule containing a composition that included 25 mg ribavirin and 100 mg minocycline was orally administered to the patient twice daily for seven days. The patient was also administered acetaminophen as needed. The patient was afebrile within three days, the patient's shortness of breath and abdominal pain decreased significantly within three days, and the patient's cough decreased significantly within five days. The patient was mostly recovered with the exception of a mild cough and slight fatigue within seven days after starting treatment.

A fifty-five year old male patient who had tested positive for COVID-19 via PCR was treated using a combination of ribavirin and minocycline. The patient had a moderate cough and severe shortness of breath when the treatment was started. A capsule containing a composition that included 25 mg ribavirin and 100 mg minocycline was orally administered to the patient twice daily for seven days. The patient was also administered acetaminophen as needed. The patient's shortness of breath improved dramatically within three days. The patient was fully recovered within seven days after starting treatment.

A twenty year old male patient with no known co-morbidities who had tested positive for COVID-19 was treated using a combination of ribavirin and minocycline. A capsule containing a composition that included 10 mg ribavirin and 100 mg minocycline was orally administered to the patient twice daily for five days. The patient was afebrile within 2-3 hours of receiving the first dose and was fully recovered within seven days following the start of treatment.

The twenty year old male patient was quarantined at home with his fifty-eight year old mother. The mother was also hypertensive and was using lisinopril for treatment of her hypertension. The mother began exhibiting symptoms of COVID-19, including shortness of breath, and was treated using a combination of ribavirin and minocycline. A capsule containing a composition that included 10 mg ribavirin and 100 mg minocycline was orally administered to the mother twice daily for five days. The mother was afebrile shortly after receiving the first dose and was fully recovered within seven days following the start of treatment.

A fifty-six year old male patient who developed symptoms of COVID-19, including shortness of breath, was treated using a combination of ribavirin and minocycline. A capsule containing a composition that included 10 mg ribavirin and 100 mg minocycline was orally administered to the patient twice daily for five days. Prior to treatment, the patient had a mild fever and an oxygen saturation level of 89% on ambient air. The patient was afebrile shortly after receiving the first dose, and the patient's oxygen saturation level improved to 92% within a few hours of receiving the first dose. On the second day after treatment was started, the patient's oxygen saturation level had improved to 96%. By the seventh day after treatment was started, the patient's oxygen saturation level had improved to 98% on ambient air and the patient reported no shortness of breath.

The previous description of the disclosed embodiments is provided to enable any person skilled in the art to make or use the invention disclosed herein. Although the various inventive aspects are disclosed in the context of one or more illustrated embodiments, implementations, and examples, it should be understood by those skilled in the art that the invention extends beyond the specifically disclosed embodiments to other alternative embodiments and/or uses of the invention and obvious modifications and equivalents thereof. It should be also understood that the scope of this disclosure includes the various combinations or sub-combinations of the specific features and aspects of the embodiments disclosed herein, such that the various features, modes of implementation, and aspects of the disclosed subject matter may be combined with or substituted for one another. The generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

All references cited are hereby expressly incorporated herein by reference.

What is claimed is:

1. A method of treatment for coronavirus disease 2019 (COVID-19) comprising administering a therapeutically effective dose of a combination of ribavirin and minocycline.

2. The method of claim 1 comprising an amount of ribavirin between 1 mg and 1200 mg and an amount of minocycline between 10 mg and 400 mg.

3. The method of claim 1 comprising an amount of ribavirin between 5 mg and 200 mg and an amount of minocycline between 50 mg and 150 mg.

4. The method of claim 1 comprising an amount of ribavirin between 5 mg and 100 mg and an amount of minocycline between 80 mg and 120 mg.

5. The method of claim 1 comprising an amount of ribavirin between 9 mg and 55 mg and an amount of minocycline between 90 mg and 110 mg.

6. The method of claim 1 comprising an amount of ribavirin between 15 mg and 30 mg and an amount of minocycline between 90 mg and 110 mg.

7. The method of claim 1 wherein the therapeutically effective dose of ribavirin and minocycline is administered as a composition comprising ribavirin and minocycline.

8. A method of treatment for coronavirus disease 2019 (COVID-19) comprising administering separately a therapeutically effective dose of ribavirin and a therapeutically effective dose of minocycline in any order.

* * * * *